US009901405B2

United States Patent
Valin et al.

(10) Patent No.: US 9,901,405 B2
(45) Date of Patent: Feb. 27, 2018

(54) MEMS-BASED METHOD AND SYSTEM FOR TRACKING A FEMORAL FRAME OF REFERENCE

(75) Inventors: Myriam Valin, Laval (CA); Catherine Proulx, Verdun (CA); Louis-Philippe Amiot, Hampstead (CA); Bruno Falardeau, Verdun (CA); Julie Deslongchamps, Brossard (CA)

(73) Assignee: ORTHOSOFT INC. (CA)

( * ) Notice: Subject to any disclaimer, the term of this patent is extended or adjusted under 35 U.S.C. 154(b) by 248 days.

(21) Appl. No.: 12/843,375

(22) Filed: Jul. 26, 2010

(65) Prior Publication Data

US 2011/0218458 A1 Sep. 8, 2011

Related U.S. Application Data

(60) Provisional application No. 61/309,585, filed on Mar. 2, 2010.

(51) Int. Cl.
*A61B 5/103* (2006.01)
*A61B 34/20* (2016.01)

(52) U.S. Cl.
CPC ...... *A61B 34/20* (2016.02); *A61B 2034/2048* (2016.02)

(58) Field of Classification Search
CPC .......... A61B 19/522; A61B 2019/5248; A61B 5/4528; A61B 5/1071; A61B 5/103
USPC ...... 600/595, 429, 587; 606/130, 87, 90, 53; 702/19
See application file for complete search history.

(56) References Cited

U.S. PATENT DOCUMENTS

| | | | |
|---|---|---|---|
| 6,122,538 A | | 9/2000 | Sliwa, Jr. et al. |
| 7,395,167 B2 * | | 7/2008 | Frolik ........................... 702/113 |
| 8,057,482 B2 * | | 11/2011 | Stone ................... A61B 17/175 600/587 |
| 2004/0243148 A1 | | 12/2004 | Wasielewski |

(Continued)

FOREIGN PATENT DOCUMENTS

| | | |
|---|---|---|
| WO | 2005/023110 | 3/2005 |
| WO | 2006/079211 | 8/2006 |

(Continued)

*Primary Examiner* — Daniel Cerioni
(74) *Attorney, Agent, or Firm* — Norton Rose Fulbright Canada LLP

(57) ABSTRACT

A system for tracking a femoral frame of reference in computer-assisted surgery comprises a sensor unit. The sensor unit is adapted to be secured to the femur. The sensor unit comprises accelerometer and gyroscope sensors that produce orientation data. A processing unit receives gyroscope and accelerometer data. The processing unit comprises a gyroscope-data calculator to provide calculated acceleration data resulting from movements of the femur, an accelerometer-data calculator to calculate measured acceleration data resulting from movements of the femur, and an acceleration comparator to relate an orientation of the sensor unit to the femur to define a femoral frame of reference. The femoral frame of reference is defined from the comparison between the calculated and the measured acceleration data. A sensor orientation interface provides orientation data for the femur from a tracking of the femoral frame of reference. A method for tracking a femoral frame of reference is also provided.

16 Claims, 2 Drawing Sheets

(56) References Cited

U.S. PATENT DOCUMENTS

| | | | |
|---|---|---|---|
| 2005/0010139 A1* | 1/2005 | Aminian | A61B 5/1038 600/595 |
| 2006/0293614 A1 | 12/2006 | Radinsky et al. | |
| 2007/0032748 A1 | 2/2007 | McNeil et al. | |
| 2007/0051910 A1 | 3/2007 | Kimura et al. | |
| 2007/0225731 A1 | 9/2007 | Couture et al. | |
| 2007/0287911 A1* | 12/2007 | Haid et al. | 600/429 |
| 2008/0091373 A1* | 4/2008 | McGibbon | A61B 5/1121 702/95 |
| 2008/0208081 A1 | 8/2008 | Murphy et al. | |
| 2008/0214960 A1* | 9/2008 | Hodgson et al. | 600/587 |
| 2009/0099570 A1* | 4/2009 | Paradis | A61B 19/5244 606/91 |
| 2009/0125117 A1 | 5/2009 | Paradis et al. | |
| 2009/0248044 A1* | 10/2009 | Amiot et al. | 606/130 |
| 2009/0265671 A1* | 10/2009 | Sachs et al. | 715/863 |
| 2011/0028865 A1* | 2/2011 | Luinge | A61B 5/1038 600/595 |
| 2011/0160738 A1* | 6/2011 | McIntosh et al. | 606/102 |

FOREIGN PATENT DOCUMENTS

| | | |
|---|---|---|
| WO | 2008/009136 | 1/2008 |
| WO | 20090117832 A1 | 10/2009 |
| WO | WO2009117833 A1 | 10/2009 |
| WO | 2010/030809 | 3/2010 |

\* cited by examiner

MEMS-BASED METHOD AND SYSTEM FOR TRACKING A FEMORAL FRAME OF REFERENCE

CROSS-REFERENCE TO RELATED APPLICATION

The present patent application claims priority on U.S. Patent Application No. 61/309,585, filed on Mar. 2, 2010, and incorporated herein by reference.

FIELD OF THE APPLICATION

The present application relates to computer-assisted orthopedic surgery using microelectromechanical sensors (MEMS).

BACKGROUND OF THE ART

One of the essential steps in navigating a bone with MEMS sensors is to locate the bone relative to the sensors. For the femur, the orientation of the sensor relative to the lateral axis can be constrained mechanically, for instance, with claws inserted under the posterior condyles so that the sensor lateral axis is aligned with the lateral axis of the bone. However, the orientation of the sensor relative to the femoral mechanical axis is more complex, as one of the anatomical landmarks defining the axis, the femoral head, is hidden inside the hip.

In an optical navigation system, the femoral head is located by moving the femur and, assuming the pelvis is stable, finding the fixed pivot point around which the bone rotates. This relies on the optical sensor having six degrees of freedom (DOF), i.e., 3DOF in position and 3DOF in orientation.

However, in a MEMS system, sensors do not automatically provide 6DOF. The 6DOF can be retrieved by integrating gyroscope and accelerometer readings—a standard technique called "dead reckoning"—but this technique is very sensitive to sensor errors and thus ill suited to low-cost sensors. Other gyroscope-based methods for retrieving the axis of the femur based on an axial rotation kinematic exist. However, such methods require a very specific and not natural leg motion, which might be difficult to apply and constrain.

SUMMARY OF THE APPLICATION

It is therefore an aim of the present disclosure to provide a novel method and system for defining and tracking a femoral coordinate system from MEMS-based data.

Therefore, in accordance with the present application, there is provided a system for tracking a femoral frame of reference in computer-assisted surgery, comprising: a sensor unit adapted to be secured to the femur, the sensor unit comprising an accelerometer sensor and a gyroscope sensor both producing orientation data; a processing unit receiving gyroscope data and accelerometer data and comprising a gyroscope-data calculator for providing calculated acceleration data from at least the gyroscope data resulting from movements of the femur; an accelerometer-data calculator for calculating measured acceleration data from the accelerometer data resulting from movements of the femur; and an acceleration comparator for relating an orientation of the sensor unit to the femur to define a femoral frame of reference, from the comparison between the calculated acceleration data and the measured acceleration data; a sensor orientation interface for providing orientation data for the femur from a tracking of the femoral frame of reference.

Further in accordance with the present application, there is provided a method for tracking a femoral frame of reference with a sensor unit comprising an accelerometer sensor and a gyroscope sensor secured to a femur, comprising: obtaining gyroscope readings and accelerometer readings resulting from movements of the femur; calculating acceleration data at least from the gyroscope readings; measuring acceleration data from the accelerometer readings; comparing the calculated and the measured acceleration data; relating an orientation of the sensor unit to the femur using the comparison to define a femoral frame of reference; and tracking the femoral frame of reference from the gyroscope readings and from the accelerometer readings.

DESCRIPTION OF THE EXEMPLARY EMBODIMENTS

MEMS is used herein to refer to micro-electromechanical sensors, such as accelerometers and gyroscopes.

CAS is used herein to refer to computer-assisted surgery.

Figure 1:
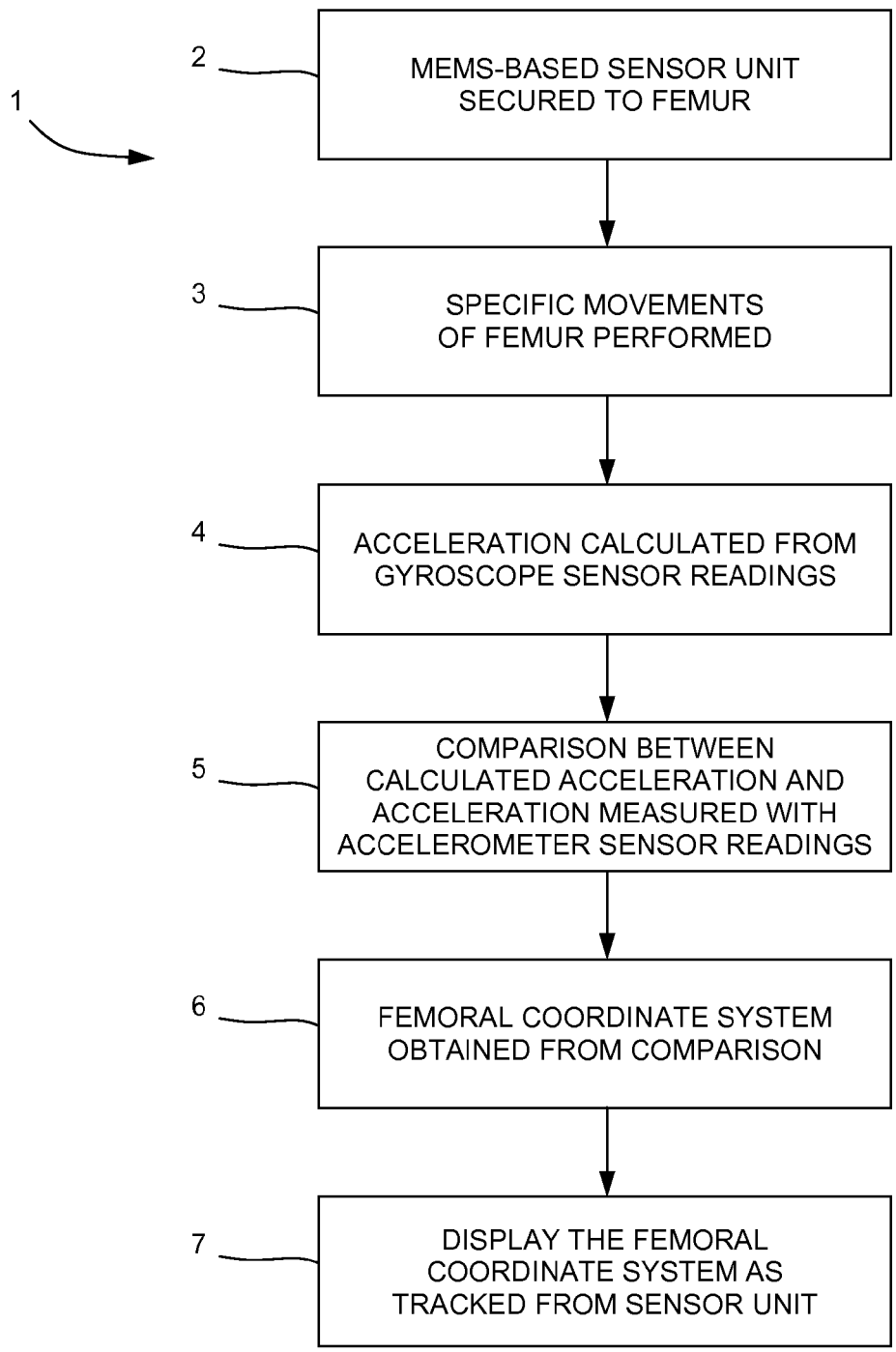
FIG. 1 is a flowchart illustrating a method for defining a femoral coordinate system with respect to a MEMS-based sensor unit, in accordance with an embodiment of the present application.

Referring to the drawings and more specifically to FIG. 1, there is illustrated at 1 a method for defining a femoral coordinate system with respect to a MEMS-based sensor unit, for subsequent tracking of the femoral coordinate system, or other femoral frame of reference (e.g., the mechanical axis of the femur). As a non-restrictive example, the femoral coordinate system defined with the method described hereinafter may be used to perform subsequent operations related to the femur, for instance as described in U.S. patent application Ser. No. 12/410,884 and corresponding PCT application publication no. WO 2009/117833, incorporated herein by reference.

Figure 2:
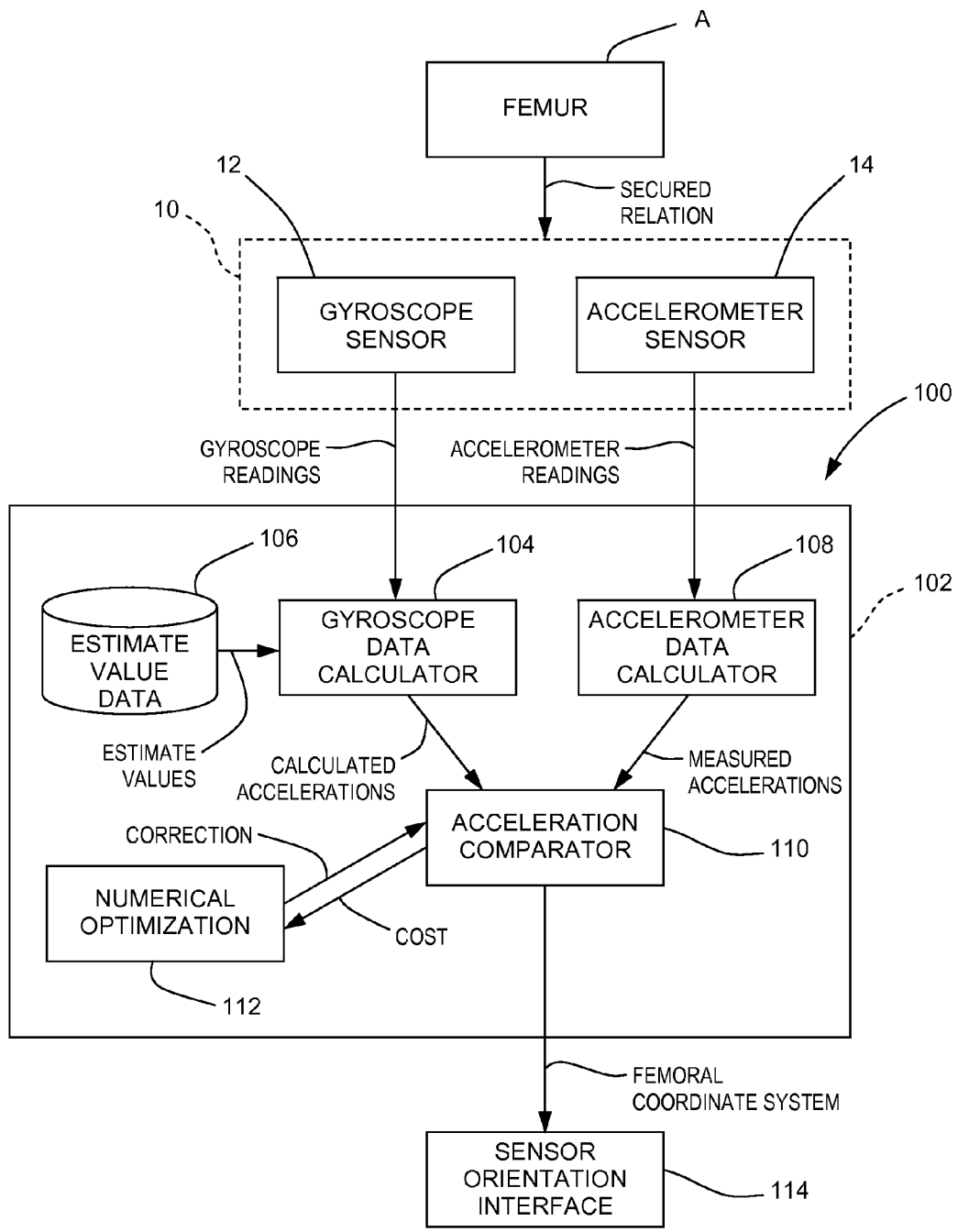
FIG. 2 is a block diagram illustrating a system for defining a femoral coordinate system with respect to a MEMS-based sensor unit, in accordance with another embodiment of the present application.

The femoral coordinate system obtained with the method 1 may be used in computer-assisted surgery (CAS), in performing alterations to the femur, to the pelvis and/or to the tibia, and in providing surgical parameters to the operator, such as limb length data. Accordingly, the method 1 may be used to find the length of the femur, i.e., the distance between the center of the femoral head and the mechanical axis entry point, in addition to tracking the femoral coordinate system from the orientation of the MEMS-based sensor unit 10 (FIG. 2).

The MEMS-based sensor unit has both a gyroscope sensor 12 and an accelerometer sensor 14 (FIG. 2), and is connected to a CAS system to provide readings from both types of sensors, by which the femoral coordinate system is defined and subsequently tracked. The gyroscope sensor 12 and the accelerometer sensor 14 each provide at least orientation data along three degrees of freedom.

According to step 2, the sensor unit 10 is secured to the femur. In an embodiment, the sensor unit 10 is secured to the mechanical entry point at the knee. When secured to the knee end of the femur, it is assumed that the movements of the sensor unit 10 are on a sphere centered on the center of the femoral head with a radius equal to the length of the femur. The best sphere that would fit the gyroscope and accelerometer readings is then found as described below.

Two elements to obtain are the orientation of the sensor unit 10 relative to a femoral coordinate system, and the radius of the sphere. If the transformation between the femur and the sensor coordinate system is represented by three successive rotations—$\lambda_1$, $\lambda_2$ and $\lambda_3$—around the x, y and z axes respectively, four parameters need to be optimized. However, when securing the sensor unit 10 to the femur, the sensor unit 10 may be aligned with the femoral posterior condyles to constrain the rotation, so that the X axis of the sensor unit 10, when projected on the femoral transverse plane, matches the X axis of the femur—$\lambda_3$ is always 0 and only three parameters need to be optimized (the radius, $\lambda_1$ and $\lambda_2$). Other relations between the sensor unit 10 and the femur are considered (e.g., using other anatomical landmark), as long as the position and orientation of the sensor unit 10 with respect to the mechanical entry point of the femur is known.

According to step 3 in FIG. 1, specific movements of the femur are performed. The gyroscope sensor 12 of the MEMS-based sensor unit 10 gives information about changes in orientation, in the form of angular velocities. The specific movements are a stopped sequence of rotations of the femur, to discriminate the effect of gravity on the measured accelerations, as described hereinafter.

In order to compute the absolute sensor orientation in world over the trajectory, the initial orientation must be known. If the sensor unit 10 is stable, $\phi$, $\zeta$ and $\theta$ can be computed from the readings of the accelerometer sensor 14. $\phi$, $\zeta$ and $\theta$ are respectively the angles between the X-, Y- and Z-axes and the ground. The afore-mentioned stopped sequence of rotations allows the $\phi$, $\zeta$ and $\theta$ angles of the gyroscope to be reinitialized. If it is assumed that the initial yaw ($\psi_0$) is 0, the initial orientation of the sensor unit 10 in the world $Sensor_{in\ world_0}$ may be computed.

According to step 4, an acceleration of the femur is calculated from the gyroscope sensor readings, and from the initial orientation of the sensor unit 10 (e.g., obtained from the accelerometer sensor 14 being stable). By the properties of the gyroscope sensor 12, an angular displacement of v*θ along the three sensor axes corresponds to an instantaneous rotation of θ radians about the unit vector v. This also applies to angular velocities. The angular velocity may be extracted during the interval and the axis around which the rotation is applied with the following equations:

$$\omega_t = |(g_x, g_y, g_z)_t|$$

$$v_t = \frac{(g_x, g_y, g_z)_t}{\omega_t}$$

If it is assumed that $\omega_t$ is constant over the interval t, the angular displacement during that interval is:

$$\theta_t = \frac{\omega_t + \omega_{t-1}}{2}\Delta t$$

If this rotation expressed in terms of axis and angle is converted to a rotation matrix $R_t$, the new orientation of the sensor unit 10 is computed with the following equation:

$$Sensor_{in\ world_t} = R_t \cdot Sensor_{in\ world_{t-1}}$$

By convention, it is assumed that a particle (reference point on femur) is at the position of the mechanical axis entry point and is aligned with the femoral coordinate system. The orientation of the sensor unit 10 in the particle coordinate system ($Sensor_{in\ particle}$) corresponds directly to the mechanical axis alignment—defined by $\lambda_1$ and $\lambda_2$—and is constant for all trajectories. It can be expressed by the following matrix:

$$Sensor_{in\ particle} = \begin{bmatrix} \cos(\lambda_1) & \sin(\lambda_1)*\sin(\lambda_2) & \cos(\lambda_2)*\sin(\lambda_1) \\ 0 & \cos(\lambda_2) & -\sin(\lambda_2) \\ -\sin(\lambda_1) & \cos(\lambda_1)*\sin(\lambda_2) & \cos(\lambda_1)*\cos(\lambda_2)] \end{bmatrix}$$

This transformation applies if the rotation is constrained by aligning the sensor unit 10 with the posterior condyles and should be modified if it is constrained by aligning, for instance, the sensor unit 10 with the antero-posterior axis.

With the relation between the sensor unit 10 and the particle being known, the orientation of the particle in the world coordinate system can be computed directly from the sensor unit's orientation using:

$$Particle_{in\ world_t} = Sensor_{in\ world_t} * Particle_{in\ sensor}$$

$$Particle_{in\ world_t} = Sensor_{in\ world_t} * Sensor_{in\ particle}^{-1}$$

By definition, the femoral mechanical axis corresponds to the Z axis of the femoral coordinate system, i.e.:

$$MechAxis_{in\ world_t} = Particle_{in\ world_t} * \begin{bmatrix} 0 \\ 0 \\ 1 \end{bmatrix}$$

where $MechAxis_{in\ world_t}$ is a 3×1 vector.

If it is assumed that the center of the femoral head is at the origin of the world, i.e., (0,0,0), the position of the particle is given by:

$$p_t = -radius * MechAxis_{in\ world_t}$$

The calculated acceleration of the particle is calculated using the equations of motion:

$$v_t = \frac{2*(p_t - p_{t-1})}{\Delta t} - v_{t-1}$$

$$a_t = \frac{v_t - v_{t-1}}{\Delta t}$$

wherein $a_t$ is the tangential acceleration (or linear acceleration [i.e., assuming that the centripetal acceleration is not part of the linear acceleration)].

In order to calculate these values, estimated values are provided for the femur radius and for the initial sensor trajectory. It is assumed that the initial velocity ($v_0$) and acceleration ($a_0$) are 0.

According to step 5, the particle acceleration measured from the gyroscope sensor 12 is compared to the readings of the accelerometer sensor 14, to determine the error (i.e., cost). The cost of the solution candidate is based on the error between the accelerations observed by the accelerometers ($a_{obs}$) and the ones calculated from the particle motion (calculated accelerations). The acceleration perceived by the sensor unit 10 includes the acceleration of the particle as well as the gravitational acceleration, whereby the stopped sequence of motions are performed with the femur to discriminate the gravitational accelerations from the other accelerations. Using the calculated orientation of the sensor unit 10, the expected acceleration ($a_{exp}$) is obtained by projecting these two accelerations on the sensor axes as follows:

$$a_{x\ exp_t} = (0,0,G) \cdot \text{Sensor}_{x\ in\ world_t} + a_{x_t} \cdot \text{Sensor}_{x\ in\ world_t}$$

$$a_{y\ exp_t} = (0,0,G) \cdot \text{Sensor}_{y\ in\ world_t} + a_{y_t} \cdot \text{Sensor}_{y\ in\ world_t}$$

$$a_{z\ exp_t} = (0,0,G) \cdot \text{Sensor}_{z\ in\ world_t} + a_{z_t} \cdot \text{Sensor}_{z\ in\ world_t}$$

where G is the gravitational constant.

The cost is defined as the least square error of the difference between the calculated and measured accelerations, as expressed by the equation:

$$\text{cost} = \sum_{t=0}^{n-\Delta t} \sqrt{\begin{matrix}(a_{x\ obs_t} - a_{x\ exp_t})^2 + \\ (a_{y\ obs_t} - a_{y\ exp_t})^2 + \\ (a_{z\ obs_t} - a_{z\ exp_t})^2\end{matrix}}$$

where n is the duration of the trajectory and $\Delta t$ is the time interval between two acquisitions.

Because some data, or parts of data, are more likely to be exact or discriminative, weighting factors are applied to the cost. Since the error in orientation (drift) increases with the time, more weight is given to the error at the beginning of the trajectory. The cost equation then becomes:

$$\text{cost} = \sum_{t=0}^{n-\Delta t} \frac{n-t}{n} * \sqrt{\begin{matrix}(a_{x\ obs_t} - a_{x\ exp_t})^2 + \\ (a_{y\ obs_t} - a_{y\ exp_t})^2 + \\ (a_{z\ obs_t} - a_{z\ exp_t})^2\end{matrix}}$$

Another way to improve the cost function is to penalize solutions that do not correspond to realistic—or possible—setups, or that do not fit complementary information. In the method, unlikely—or impossible—radii and mechanical axis alignments are penalized. If the radius is below or over a defined threshold (for example, below 40 cm or over 60 cm), a penalization, proportional to the difference, is applied. The penalization is added to the total cost and is expressed as follows:

if radius>Radius$_{max}$→cost$_{radius}$=(Radius$_{max}$−radius) *k$_{radius}$ if radius<Radius$_{min}$→cost$_{radius}$=(radius−Radius$_{min}$) *k$_{radius}$ where k$_{radius}$ is the radius penalization constant. The same penalization if applied if $\lambda_1$ or $\lambda_2$ are over a defined threshold.

As an alternative method for calculating the tangential acceleration (step 4) and comparing this alternative tangential acceleration with the readings of the accelerometer sensor 14, the tangential acceleration $a_t$ of the particle may be calculated without using the equations of motion described above, and thus without depending on acquisition time.

This alternate calculation method and cost function stem from the principle that, when a particle is rotating around a fixed center of rotation, the perceived acceleration comes from three different sources. One first source is the centripetal acceleration, $\vec{a}_c$. The centripetal acceleration is a function of current angular velocity and of the radius, namely the acceleration required to keep the moving particle on its spherical trajectory. A second source is the tangential acceleration, $\vec{a}_t$. This is the acceleration required to change the angular velocity of the particle through time. A third source is gravity, $\vec{a}_g$. While not an actual force affecting the displacement of the particle (if it were the case, it would not stay on a spherical trajectory), it is nonetheless perceived by the accelerometer sensor 14. This is function of G and the current tilt attitude of the device.

According to the alternative steps 4 and 5, it is required to find values of $\lambda_1$ and $\lambda_2$ which, if applied to the sensor unit 10, will orient it so that its Z axis is aligned with the mechanical axis.

Accordingly:

$$\vec{\text{MechAxis}}_{in\ sensor} = \text{particle}_{in\ sensor} * \vec{\text{MechAxis}}_{in\ particle}$$

$$\vec{\text{MechAxis}}_{in\ sensor} = \text{sensor}^{-1}_{in\ particle} * \vec{\text{MechAxis}}_{in\ particle}$$

$$\vec{\text{MechAxis}}_{in\ sensor} = \begin{bmatrix} \cos(\lambda_1) & 0 & -\sin(\lambda_1) \\ \sin(\lambda_1)*\sin(\lambda_2) & \cos(\lambda_2) & \cos(\lambda_1)*\sin(\lambda_2) \\ \cos(\lambda_2)*\sin(\lambda_1) & -\sin(\lambda_2) & \cos(\lambda_1)*\cos(\lambda_2) \end{bmatrix} \begin{bmatrix} 0 \\ 0 \\ 1 \end{bmatrix}$$

$$\vec{\text{MechAxis}}_{in\ sensor} = \begin{bmatrix} -\sin(\lambda_1) \\ \cos(\lambda_1)*\sin(\lambda_2) \\ \cos(\lambda_1)*\cos(\lambda_2) \end{bmatrix}$$

From this estimated mechanical axis, and the instantaneous readings of the gyroscope sensor 12 ($\vec{g}_t$), it is possible to extract the angular velocity around the spherical trajectory ($\omega'_t$). This is done by subtracting the component of the perceived angular velocity around the mechanical axis. In order to achieve this, the perceived rotation vector must be projected onto the tangential plane.

$$\omega'_t = |\vec{g}_t - \text{proj}(\vec{g}_t, \vec{\text{MechAxis}}_{in\ sensor})|$$

$$\omega'_t = |\vec{g}_t - (\vec{\text{MechAxis}}_{in\ sensor} * (\vec{\text{MechAxis}}_{in\ sensor} \cdot \vec{g}_t))|$$

Knowing the amplitude of the angular body $\omega'_t$ and then using the estimated radius which is fixed in time, the current centripetal acceleration applied to the particle may be extracted.

$$\vec{a}_{ct} = r\omega'^2_t * \vec{\text{MechAxis}}_{in\ sensor}$$

As described earlier, it is possible from an initial inclination of a particle, to use the angular velocities to track the orientation of the particle through time. In the present case, the inclination of the sensor unit 10 may be calculated as:

$$\phi_t = \text{Sensor}_{in\ worldx3_t}$$

$$\zeta_t = \text{Sensor}_{in\ worldy3_t}$$

$$\theta_t = \text{Sensor}_{in\ worldz3_t}$$

Knowing the inclination of the sensor unit 10 at a moment, the acceleration perceived by the sensor unit 10 due to gravity can be calculated.

$$\vec{a}_{g_t} = G * \begin{bmatrix} \sin(\phi_t) \\ \sin(\zeta_t) \\ \sin(\theta_t) \end{bmatrix}$$

As mentioned earlier, it is expected that, at all times, the acceleration perceived by the MEMS sensor unit 10 ($\vec{a}_p$) should be the sum of the gravity ($\vec{a}_g$), the centripetal acceleration ($\vec{a}_c$) and the tangential acceleration ($\vec{a}_t$). With reliable estimates of both the gravity and centripetal acceleration values, the tangential acceleration vector may be calculated.

For the comparison of step 5, by definition, the tangential acceleration vector should be perpendicular to the mechanical axis. A suitable cost function can thus be described as the sum of the perceived tangential acceleration projected onto the mechanical axis.

$$\text{cost} = \sum_{t=0}^{n-\Delta t} (\vec{a}_{t_t}) \cdot \vec{MechAxis}_{in\ sensor}$$

$$\text{cost} = \sum_{t=0}^{n-\Delta t} (\vec{a}_{p_t} - \vec{a}_{g_t} - \vec{a}_{c_t}) \cdot \vec{MechAxis}_{in\ sensor}$$

Minimizing this cost function will give the $\lambda_1$ and $\lambda_2$ values corresponding to the axis between the acceleration sensor and the spherical pivot point. In the present case, where the accelerometer sensor 14 is positioned at the mechanical axis entry point, this equates to the femoral mechanical axis.

According to step 6, the femoral coordinate system is obtained, by the orientation of the sensor unit 10 being known relative to the femur. The femoral coordinate system is obtained by numerical optimization from either one of the cost functions described above depending on the method for calculating the particle acceleration, or any other appropriate cost function. The numerical optimization may be performed using the Matlab™ fminsearch function, or using known algorithms such as gradient descent, simulated annealing, etc. In addition to obtaining the orientation of the sensor unit 10 relative to the femur, additional data may be obtained in 6, such as the real trajectory of the particle, and the radius of the particle. The radius of the particle may be used subsequently to calculate parameters such as limb length discrepancy.

According to step 7, the femoral coordinate system is displayed, as tracked from the readings of the sensor unit 10. For instance, the femoral coordinate system is displayed as axes on a screen. Alternatively, the femoral coordinate system is displayed by way of LED indicators showing a proper orientation of the tools connected to the sensor unit 10. For instance, the sensor unit 10 may be connected to a cutting block, as described in U.S. patent application Ser. No. 12/410,884 and corresponding PCT application publication no. WO 2009/117833. A proper orientation of the cutting block in terms of varus-valgus may be displayed by confirmatory lights on the sensor unit 10/cutting block as the orientation of the cutting block is adjusted.

In order to optimize the precision of the method, the following optimizations may be applied during the steps of the method 1:

Movements may be short in order to reduce the drift in orientation (due to the integration of the noisy gyroscope readings).

Movements may be in at least two directions (for example, horizontal and vertical) so that they fit only one sphere, and thus only one solution exists.

It may be desired to use filters to reduce noise in the accelerometer and gyroscope readings. The filtering may be done directly by the sensor unit 10, using hardware components, or within a processing unit, as described hereinafter.

The acquisition rate should be fast enough to allow filtering and to respect the assumption that the acceleration is constant over some time intervals.

The sensor unit 10 must be stable at the beginning of each sequence in order to know its initial inclination (having the device stable at the end of the sequence could also be used to improve the algorithm).

The sensor unit 10 is aligned in rotation with the femur, which allows the sensor orientation of the femur coordinate system from $\lambda_1$ and $\lambda_2$ to be calculated.

The accelerometer sensor 14 may be fixed at the position of the mechanical axis entry point.

Large accelerations might help discriminate between solutions if the noise does not increase with the acceleration.

The cost function may be improved, for instance by adding weighting factors (e.g., add weight to trajectories where the final orientation computed from gyroscope readings fit the final inclination computed from the accelerometer readings) and penalization (e.g., penalize solutions for which the final velocity is not null, assuming that the sensor unit 10 is stable at the end of the trajectory).

Referring to FIG. 2, a system for defining a femoral coordinate system with respect to a MEMS-based sensor unit, is generally shown at 100, and comprises the sensor unit 10 equipped with the gyroscope sensor 12 and the accelerometer sensor 14. The sensor unit 10 is fixed to the femur A, for instance as described for method 1.

A CAS processing unit 102 receives the readings from the sensor unit 10 to define the femoral coordinate system, i.e., a relation between the femur and the orientation of the sensor unit 10 is defined for subsequently tracking the femur from the readings of the sensor unit 10. The CAS processing unit 102 comprises a processor and appropriate applications to define the femoral coordinate system, for instance as described by method 1.

The processing unit 102 comprises a gyroscope data calculator 104. The gyroscope data calculator 104 calculates an initial sensor orientation and thus calculated accelerations along the three axes of the gyroscope sensor 12, when the femur moves in the manner described for method 1. In order to calculate, these parameters, the processing unit 102 must use estimate values for an initial sensor orientation (e.g., in the 2 degrees of freedom $\lambda_1$ and $\lambda_2$) and for an initial femur radius. In one embodiment, these estimate values are provided by the estimate value database 106. Because of errors due to noise on gyroscope readings and of the acquisition times, the accelerations may need to be filtered to reduce the ripples. A zero-phase low-pass filter may be used, but other filter types may be used as well.

The accelerometer data calculator 108 receives readings from the accelerometer sensor 14, and calculates the measured accelerations for the sensor unit 10.

The calculated accelerations from the gyroscope data calculator 104, and the measured accelerations from the accelerometer data calculator 108 are compared by the acceleration comparator 110. Accordingly, the acceleration comparator 110 measures a validity of the estimate values in producing a solution cost. The solution cost is then used in a numerical optimization application 112 by the acceleration comparator 110, to obtain the sensor orientation relative to the femur, and thus to define the femoral coordinate system for subsequent tracking with readings of the sensor unit 10. Additionally, the acceleration comparator 110 may calculate other surgical parameters, such as a real trajectory of the femur and the radius of the femur.

A sensor orientation interface 114 displays data pertaining to the femoral coordinate system. The interface 114 may be a monitor, indicator lights, sound signals, that provide orientation data related to the relation between the femur and tracked tools.

The invention claimed is:

1. A system for tracking a femoral frame of reference in computer-assisted surgery, comprising:
    a sensor unit adapted to be secured to a distal end of a femur, the sensor unit comprising an accelerometer sensor and a gyroscope sensor both configured for producing orientation data;
    a processing unit configured for receiving gyroscope data and accelerometer data and comprising:
        a gyroscope-data calculator for providing calculated acceleration data using at least gyroscope data resulting from movements of the femur about a proximal end thereof;
        an accelerometer-data calculator for calculating measured acceleration data using accelerometer data resulting from the movements of the femur; and
        an acceleration comparator for relating an orientation of the sensor unit to the femur to define the femoral frame of reference, the acceleration comparator performing a numerical optimization to determine the orientation of the sensor unit, the numerical optimization using at least a plurality of estimated radius values between the proximal end and the distal end of the femur with the calculated acceleration data and the measured acceleration data to determine a radius value corresponding to the acceleration data and the measured acceleration data at the distal end of the femur;
    a sensor orientation interface for providing orientation data for the femur from a tracking of the femoral frame of reference.

2. The system according to claim 1, wherein the gyroscope-data calculator provides the calculated acceleration data using an estimated trajectory value and the estimated radius values for the femur.

3. The system according to claim 1, wherein the gyroscope-data calculator provides the calculated acceleration data using the estimated radius values for the femur for deducting centripetal accelerations from the gyroscope data, and using an orientation of the gyroscope sensor for deducting gravity from the accelerometer data.

4. The system according to claim 1, wherein the femoral frame of reference defined by the acceleration comparator is a three-axis femoral coordinate system.

5. The system according to claim 1, wherein the acceleration comparator calculates at least one of a femur length and a femoral trajectory.

6. The system according to claim 1, further comprising filters in any one of the sensor unit and the processing unit to reduce noise from any one of the gyroscope data and the accelerometer data.

7. A method for tracking with a tracking system a femoral frame of reference with a sensor unit comprising an accelerometer sensor and a gyroscope sensor secured to a femur, comprising:
    obtaining with the tracking system gyroscope readings and accelerometer readings from the sensor unit and resulting from movements of the femur;
    calculating acceleration data with the tracking system using at least the gyroscope readings;
    measuring acceleration data with the tracking system using the accelerometer readings;
    comparing with the tracking system the calculated and the measured acceleration data using at least a plurality of estimated radius values in a numerical optimization to determine a radius value corresponding to the calculated acceleration data and the measured acceleration data at a distal end of the femur, whereby an orientation of the sensor unit is related to the femur;
    relating with the tracking system the orientation of the sensor unit to the femur using the comparison to define the femoral frame of reference; and
    tracking with the tracking system the femoral frame of reference from the gyroscope readings and from the accelerometer readings.

8. The method according to claim 7, wherein calculating acceleration data comprises using an estimated value for a trajectory of the femur and the estimated radius values of the femur.

9. The method according to claim 7, wherein calculating acceleration data comprises using the estimated radius values for a radius of the femur for deducting a centripetal acceleration from the gyroscope readings, and obtaining an orientation of the gyroscope to deduct the gravity from the accelerometer readings.

10. The method according to claim 7, further comprising calculating at least one of a radius of the femur and a trajectory of the femur from the frame of reference.

11. The method according to claim 7, wherein defining the femoral frame of reference comprises defining a three-axis coordinate system.

12. The method according to claim 7, wherein the method is performed on a bone model or cadaver.

13. The method according to claim 7, wherein defining the femoral frame of reference comprises setting an axis of the femoral frame of reference on a mechanical axis of the femur.

14. The method according to claim 7, further comprising displaying information pertaining to an orientation of a tool relative to the tracked femoral frame of reference.

15. The method according to claim 14, wherein displaying information pertaining to an orientation of a tool relative to the tracked femoral frame of reference comprises displaying information indicative of a varus-valgus value of the tool.

16. The system according to claim 1, wherein the numerical optimization is performed by using one of a gradient descent algorithm and a simulated annealing algorithm.

* * * * *